United States Patent [19]
Nishiki et al.

[11] Patent Number: 5,441,879
[45] Date of Patent: Aug. 15, 1995

[54] METHOD FOR STABILIZING ANTIGENICITY OF MYELOPEROXIDASE BY INCUBATING WITH CYCLODEXTRIN

[75] Inventors: Nobuo Nishiki, Otsu; Kazumi Horiuchi, Hikone, both of Japan

[73] Assignee: Nissho Corporation, Osaka, Japan

[21] Appl. No.: 186,646

[22] Filed: Jan. 26, 1994

[30] Foreign Application Priority Data

Jan. 29, 1993 [JP] Japan .................................. 5-34271

[51] Int. Cl.⁶ .......................... C12N 9/96; C12N 9/08; C08B 37/16; A61K 31/735
[52] U.S. Cl. .................................... 435/188; 435/7.1; 435/174; 435/192; 436/518; 536/103; 536/124
[58] Field of Search ................... 514/58; 536/103, 124; 435/188, 192, 4, 7.1, 174; 436/518

[56] References Cited

U.S. PATENT DOCUMENTS

| | | | |
|---|---|---|---|
| 4,228,240 | 10/1980 | Dawson et al. | 435/188 |
| 4,252,896 | 2/1981 | Shaffar | 435/7 |
| 4,306,025 | 12/1981 | Hasegawa et al. | 435/192 |
| 4,647,532 | 3/1987 | Watanabe et al. | 435/28 |
| 5,183,809 | 2/1993 | Weisz et al. | 514/58 |
| 5,298,410 | 3/1994 | Phillips et al. | 435/188 |

FOREIGN PATENT DOCUMENTS

| | | |
|---|---|---|
| 0303062 | 2/1989 | European Pat. Off. . |
| 0340068 | 11/1989 | European Pat. Off. . |
| 59-104556 | 6/1984 | Japan . |
| 1-117786 | 5/1989 | Japan . |
| 1117786 | 5/1989 | Japan . |
| 90/03784 | 4/1990 | WIPO . |

OTHER PUBLICATIONS

Sigma Chemie—Biochemicalien Organische Verbindingen voor Research en Diagnostica—1992—p. 692 "Myeloperoxidase"—Brussels.

Journal of Immunological Methods—Determination of anti–neutrophil cytoplasm antibodies (ANCA) specificity by immunofluorescence on chronic myelocytic leukemia cells—A. Chevailler et al, vol. 147, 1992, pp. 101–109, Amsterdam.

Izutsu et al, "Stabilization of $\beta$-galactosidase . . ." Int. J. Pharm. 90:187-194 (1993).

*Primary Examiner*—David M. Naff
*Assistant Examiner*—Francisco C. Prats
*Attorney, Agent, or Firm*—Armstrong, Westerman, Hattori, McLeland & Naughton

[57] ABSTRACT

The antigenicity of a myeloperoxidase is stabilized by applying a solution of cyclodextrin to a myeloperoxidase and incubating the myeloperoxidase with the solution of cyclodextrin. The myeloperoxidase may be immobilized on an insoluble carrier prior to applying the solution of cyclodextrin. The stabilized myeloperoxidase can be stored for a long period of time, even at high temperature, and used as a reagent in an immunoassay.

5 Claims, No Drawings

METHOD FOR STABILIZING ANTIGENICITY OF MYELOPEROXIDASE BY INCUBATING WITH CYCLODEXTRIN

BACKGROUND OF THE INVENTION

The present invention relates to a method for stabilizing antigenicity of a myeloperoxidase, and more particularly to a method for stabilizing antigenicity of an immobilized myeloperoxidase or a myeloperoxidase in solution.

A myeloperoxidase is an enzyme having hemes similar to heme a. The enzyme present in a leukocyte, mainly in a neutrophil, and carries out detoxication of bacterias and the like through halide ions.

In 1982, Davies et al. reported anti-neutrophil cytoplasmic antibodies. The antibodies were grouped into 2 subsets according to their stained pattern by indirect immunofluorescence technique (IIF). One subset is referred to as Cytoplasmic-ANCA (C-ANCA) and the other is referred to as Perinuclear-ANCA (P-ANCA). The myeloperoxidase is one of antigens for P-ANCA, thus it became to be utilized as an antigen having immunological functions.

In recent years, it has been noticed that quantification of an anti-neutrophil cytoplasmic antibody, such as P-ANCA, in a blood examination is useful for a diagnosis of renal diseases. Thus, a kit for enzyme immunoassay (EIA) including a myeloperoxidase as the antigen in the antigen-antibody reaction is commercially available. The enzyme immunoassay is carried out by the following procedure: First, the myeloperoxidase is allowed to adhere to an insoluble carrier such as a surface of synthetic resin plate by adsorption or the like, and to be dried. Next, a sample such as serum is applied to the above-mentioned carrier on which the myeloperoxidase is immobilized. A chromophore reagent or the like is added thereto, and then, the absorbance is measured.

However, since the antigenicity, namely the immunological property, of myeloperoxidase is unstable and easy to dissapear in any form, such as in a form of immobilized enzyme and in a form of aqueous solution, except in a form of freeze-dried powder, the myeloperoxidase cannot be stored for a long period such as more than 3 months. Therefore, once a solution of myeloperoxidase or an immobilized enzyme is prepared as a reagent, the reagent must be used thoroughly, otherwise the remaining reagent cannot be used later. The myeloperoxidase has a defect that a prepared reagent thereof is likely to be wasted.

An object of the invention is to provide a method for stabilizing antigenicity of a myeloperoxidase, particularly an immobilized myeloperoxidase or a solution of myeloperoxidase for a long period such as more than 6 months.

This and the other objects of the present invention will become apparent from the description hereinafter.

SUMMARY OF THE INVENTION

In accordance with the present invention there is provided a method for stabilizing antigenicity of a myeloperoxidase which comprises applying a solution of cyclodextrin to a myeloperoxidase and incubating the myeloperoxidase with the solution of cyclodextrin.

According to the invention, prolonged stabilization of myeloperoxidase antigenicity is provided. Therefore, a reagent of myeloperoxidase which has been stored, even at the high temperature, for a long period can be used, by which precise examination is achieved. Accordingly, a myeloperoxidase reagent can be utilized effectively, without any waste.

DETAILED DESCRIPTION

In the present invention, a cyclodextrin is utilized as a stabilizer for antigenicity. Cyclodextrins are cyclic polysaccharides wherein at least 6 glucose molecules linked with each other by $\alpha(1\rightarrow 4)$ glucosidic bonds. Until now, there have been known $\alpha$-cyclodextrin consisting of 6 units of glucose, $\beta$-cyclodextrin consisting of 7 units, $\gamma$-cyclodextrin of 8 units, $\delta$-cyclodextrin of 9 units and branched cyclodextrin wherein glucose or larger $\alpha$-1,4-glucan molecules are linked at the ring. Any kind of cyclodextrin, that is, $\alpha$-cyclodextrin, $\beta$-cylodextrin, $\gamma$-cyclodextrin, $\delta$-cyclodextrin or branched cylodextrin, or arbitrary combination thereof in arbitrary ratio can be used in the method of the present invention.

A solution of cyclodextrin is applied to a myeloperoxidase. Then, the myeloperoxidase is incubated with the solution of cyclodextrin. The incubation is carried out, preferably at 4° to 30° C. for 15 to 300 min.

In the present invention, the concentration of cyclodextrin in the incubation system is at least 0.0005 w/v %. In case the $\beta$-cyclodextrin, $\gamma$-cyclodextrin or $\delta$-cyclodextrin is used, the concentration of cyclodextin in the incubation mixture is preferable at least 0.05 w/v %. Since solubilities of the cyclodextrins are different depending on the kind of the cyclodextrin, the cyclodextrin solution may be prepared within the possible concentration to prepare. For example, solubility of a cyclodextrin in water is 14.5 g/100 ml ($\alpha$-cyclodextrin), 1.85 g/100 ml ($\beta$-cyclodextrin) and 23.2 g/100 ml ($\gamma$-cyclodextrin), and $\delta$-cyclodextrin is very soluble.

As to the cyclodextrin solution, any solvent can be used, unless the solvent denaturalizes proteins. For example, a buffered solution of pH around neutral, that is pH 5 to 8, such as phosphate buffer, tris-HCl buffer or the like can be used.

As to the form of a myeloperoxidase, any form except a form of freeze-dried powder can be employed. Examples are a myeloperoxidase immobilized onto a solid carrier, an aqueous solution containing a myeloperoxidase and the like.

Generally, when a myeloperoxidase is used as the antigen in EIA, a myeloperoxidase solution is applied to an insoluble carrier to adhere to the carrier by adsorption. Instead of adsorption, the adhesion can be carried out by covalent bond method, by ionic bond method or the like. Blocking may be carried out by using bovine serum albumin, gelatin, casein or the like. After the adhesion, the myeloperoxidase is dried to be immobilized. As the insoluble carrier, glass, agarose, dextran, cellulose, polyacrylamide, polystyrene, homopolypeptide, latex, polycarbonate, polypropylene, aminoalkyl-silica glass, silicone rubber or the like can be used.

According to the present invention, the antigenicity of a myeloperoxidase can be maintained, and after long storage the decrease of antigenicity is very little. The antigenicity herein means the ability to bind with anti-myeloperoxidase antibodies, which can be measured by EIA.

The present invention is more specifically described and explained by means of the following Examples in which all per cents and parts are by weight unless otherwise noted. It is to be understood that the present invention is not limited to the Examples, and various changes and modifications may be made in the invention without departing from the spirit and scope thereof.

EXAMPLES

Into each well of microtiter plates (A/S NUNC, 96-wells) was introduced 200 μl/well of a solution of myeloperoxidase (made by Kamiya Biomedical Company, >200 U/mg of protein) (5 μg of protein/ml of a phosphate buffer (pH 6)). The solution was allowed to stand at 4° C. for 18 hrs. Then, each well was washed with a phosphate buffer (pH 7.2) containing 0.05 w/v % Tween-20, and thereinto was introduced 200 μl of phosphate buffer (pH 7.0) solution of α-cyclodextrin, β-cyclodextrin or γ-cyclodextrin (made by NACALAI TESQUE, INC.). The final concentrations of cyclodextrin are shown in Table 1, 2 and 3 respectively. For each cyclodextrin concentration, 3 wells were used.

After incubation at 25° C. for 60 min., the solution was removed from the wells and the plates were dried in a desiccator to complete the immobilization.

The plates were stored at 40° C. until 200 μl/well of a sample solution containing anti-myeloperoxidase antibody (serum from a patient of Microscopic polyarterits nodosa, 50-fold diluted with a phosphate buffer (pH 7.3)) was introduced thereinto on day 0, day 7 and day 14 after the immobilization of myeloperoxidase.

The plates containing sample solution were incubated at 25° C. for 60 min., and each well was washed with the phosphate buffer (pH 7.2) containing 0.05% Tween-20. Then, 200 μl/well of an alkaline phosphatase labelled anti-human IgG antibody in phosphate buffer (pH 7.3) (made by Sigma Chemical Company) was introduced into the wells.

Incubation at 25° C. for 60 min. was performed. After washing with the phosphate buffer (pH 7.2) containing 0.05% Tween-20, 200 μl/well of a solution of disodium p-nitrophenylphospahte (made by Sigma Chemical Company) (1 mg/ml of diethanolamine-HCl buffer (pH 9.8)) was introduced into each well as a chromophore reagent.

At 0 min. and 60 min. after introduction of the chromophore reagent, absorbancy was measured using a microplate reader Type MTP 120 (manufactured by Corona Electric Co., LTD.) at 405 nm. Each absorbance, which is the difference between absorbance, values of 0 min. and 60 min., was employed as an indication of antigenicity.

Stability of myeloperoxidase antigenicity was examined by time-dependent alteration of residual antigenicity under the storage at 40° C., judging from each relative value (%) of absorbance calculated on the basis of the absorbance of day 0 (100%).

The results are shown in Table 1 for α-cyclodextrin, Table 2 for β-cyclodextrin and Table 3 for γ-cyclodextrin.

As a control, 3 wells in each myeloperoxidase-immobilized plate without treating with cyclodextrins were also prepared, treated and measured in the same manner as the above-mentioned. Also, the stability was examined in the same manner as the examples. Results are shown in Tables 1, 2 and 3.

As is clear from Table 1, there are differences of residual antigenicity between examples using α-cyclodextrin and control, even concerning the values of day 7 after immobilizing. Further, as to the values of day 14, the control value is declined extremely, whereas the examples retain high antigenicity at every concentration tested.

The results of Table 2 reveal that when the concentration of β-cyclodextrin is 0.05 to 2.0 w/v %, the stability of myeloperoxidase antigenicity was improved both on day 7 and day 14.

Further, as to γ-cyclodextrin, effective concentration range is 0.05 to 4.0 w/v % thereof as is clear from Table 3.

The results suggest that incubating with cyclodextrins in a proper concentration range improves stability of myeloperoxidase antigenicity even under storage at a high temperature such as 40° C.

TABLE 1

| Sample | Concentration (w/v %) | Residual antigenicity (%) | |
|---|---|---|---|
| | | day 7 | day 14 |
| α-cyclodextrin | 0 | 90.2 | 63.6 |
| | 0.0005 | 93.7 | 73.9 |
| | 0.005 | 90.3 | 73.8 |
| | 0.01 | 95.8 | 80.7 |
| | 0.05 | 94.1 | 86.0 |
| | 0.1 | 97.8 | 89.5 |
| | 1.0 | 101.6 | 94.5 |
| | 2.0 | 103.1 | 99.8 |
| | 4.0 | 104.6 | 102.0 |
| | 6.0 | 100.3 | 98.4 |
| | 8.0 | 104.3 | 97.8 |
| | 10.0 | 98.6 | 95.1 |
| | 12.0 | 101.2 | 94.6 |
| | 14.0 | 97.8 | 94.6 |

TABLE 2

| Sample | Concentration (w/v %) | Residual antigenicity (%) | |
|---|---|---|---|
| | | day 7 | day 14 |
| β-cyclodextrin | 0 | 84.7 | 73.9 |
| | 0.0005 | 77.2 | 73.3 |
| | 0.005 | 78.7 | 68.5 |
| | 0.01 | 80.2 | 70.7 |
| | 0.05 | 90.1 | 78.6 |
| | 0.1 | 99.2 | 83.0 |
| | 1.0 | 94.5 | 79.8 |
| | 2.0 | 90.3 | 74.8 |

TABLE 3

| Sample | Concentration (w/v %) | Residual antigenicity (%) | |
|---|---|---|---|
| | | day 7 | day 14 |
| γ-cyclodextrin | 0 | 83.8 | 75.6 |
| | 0.0005 | 79.4 | 73.4 |
| | 0.005 | 79.7 | 75.5 |
| | 0.01 | 79.8 | 76.3 |
| | 0.05 | 87.2 | 83.0 |
| | 0.1 | 84.5 | 83.3 |
| | 1.0 | 89.5 | 93.9 |
| | 2.0 | 94.2 | 95.9 |
| | 4.0 | 91.4 | 91.4 |

What we claim is:

1. A method for stabilizing the antigenicity of a myeloperoxidase, by maintaining the ability of the myeloperoxidase to bind to an anti-myeloperoxidase antibody, consisting essentially of incubating the myeloperoxidase with a solution of an α-, β- or γ-cyclodextrin in an amount of the cyclodextrin effective to stabilize the myeloperoxidase.

2. A method according to claim 1, wherein the myeloperoxidase incubated in the solution is immobilized onto an insoluble carrier.

3. A method according to claim 1, wherein the myeloperoxidase is dissolved in the solution.

4. A method according to claim 1, wherein the concentration of the cyclodextrin in the solution is at least 0.05 w/v %.

5. A method according to claim 1, wherein the cyclodextrin is α-cyclodextrin and the concentration of the α-cyclodextrin in the solution is at least 0.0005 w/v %.

* * * * *